US012734311B2

(12) United States Patent
Bevers et al.

(10) Patent No.: US 12,734,311 B2
(45) Date of Patent: Sep. 15, 2026

(54) APPARATUS FOR WARMING A MEDICAL DEVICE PRIOR TO USE

(71) Applicants: Michael J. Bevers, Clark, SD (US); Angela M. Bevers, Clark, SD (US)

(72) Inventors: Michael J. Bevers, Clark, SD (US); Angela M. Bevers, Clark, SD (US)

( * ) Notice: Subject to any disclaimer, the term of this patent is extended or adjusted under 35 U.S.C. 154(b) by 412 days.

(21) Appl. No.: 18/387,979

(22) Filed: Nov. 8, 2023

(65) Prior Publication Data

US 2025/0144321 A1 May 8, 2025

(51) Int. Cl.
*A61M 5/44* (2006.01)
*A61M 39/08* (2006.01)

(52) U.S. Cl.
CPC .............. *A61M 5/44* (2013.01); *A61M 39/08* (2013.01); *A61M 2205/3653* (2013.01); *A61M 2205/8206* (2013.01)

(58) Field of Classification Search
CPC .................... A61M 5/44; A61M 39/08; A61M 2205/3653; A61M 2205/8206; A61M 2205/36; A61B 2018/0212; A61F 7/007; A61F 2007/0054; A61F 2007/0055
See application file for complete search history.

(56) References Cited

U.S. PATENT DOCUMENTS 3,371,975 A 3/1968 Meltzer
4,790,181 A 12/1988 Aine
4,885,937 A 12/1989 Tanaka
5,013,889 A * 5/1991 Bakke .................... H05B 3/22 392/401
5,807,332 A * 9/1998 Augustine ............... A61M 5/44 604/113
6,129,876 A 10/2000 Qin
9,931,279 B2 4/2018 Hyun
2003/0130624 A1 7/2003 Kowalik
(Continued)

FOREIGN PATENT DOCUMENTS

CN 201814947 5/2011
WO WO-9621485 A1 * 7/1996 .............. A61M 5/44

OTHER PUBLICATIONS

3M Bair Hugger Warming Blanket System, brochure, 4 pages, 3M Medical, St. Paul, Minnesota, copyright 2016.
(Continued)

*Primary Examiner* — Wesley G Harris
(74) *Attorney, Agent, or Firm* — Jeffrey A. Proehl; Woods, Fuller, Shultz & Smith PC

(57) ABSTRACT

A system may comprise an apparatus for warming at least a portion of a medical implement. The apparatus may comprise a medical implement engaging structure for engaging the portion of the medical implement to permit transfer of heat to the implement. The engagement structure may be configured to form a pocket for receiving the implement, and may include a pair of side portions movable with respect to each other to form the pocket. The apparatus may also include a heating element on at least one of the side portions to increase a temperature of the side portion to warm a medical implement in the pocket. The apparatus may also include an attraction element on at least one of the side portions to cause attraction between the side portions to maintain the side portions in operational positions of the side portions.

19 Claims, 8 Drawing Sheets

(56) References Cited

U.S. PATENT DOCUMENTS

| | | | | |
|---|---|---|---|---|
| 2013/0174842 | A1* | 7/2013 | Young .............. | A61M 16/1075<br>128/203.14 |
| 2014/0128845 | A1* | 5/2014 | Hyun ................. | A61J 15/0026<br>604/113 |

OTHER PUBLICATIONS

3M Bair Hugger Normothermia System, brochure, 8 pages, 3M Medical, St. Paul, Minnesota, copyright 2016.

3M Bair Hugger Warming Gown System, brochure, 8 pages, 3M Medical, St. Paul, Minnesota, copyright 2016.

* cited by examiner 12
16
52
19
18
52

46
56
32
50
52
24
14
54
34
36
30
52

22
26
30
82
24
54
92
90
84
84
86

22
30
54
92
90
32

APPARATUS FOR WARMING A MEDICAL DEVICE PRIOR TO USE

BACKGROUND

Field

The present disclosure relates to medical device preparatory equipment and more particularly pertains to a new apparatus for warming a medical device prior to use to facilitate the use of the device on a patient.

SUMMARY

In one aspect, the present disclosure relates to a system that may comprise an apparatus for warming at least a portion of a medical implement. The apparatus may comprise a medical implement engaging structure for engaging the portion of the medical implement to permit transfer of heat to the implement. The engagement structure maybe configured to form a pocket for receiving the medical implement. The engagement structure may have a receiving condition and an operational condition. The receiving condition may be characterized by the pocket being substantially open, and the operational condition may be characterized by the pocket being substantially closed. The implement engaging structure may comprise a pair of side portions configured to form the pocket, with the side portions being movable with respect to each other. The side portions may each have a receiving position corresponding to the receiving condition of the engagement structure, and the side portions may each have an operational position corresponding to the operational condition of the engagement structure. The receiving position of the side portions may be characterized by the side portions being separated and moved away from each other. The operational position of the side portions may be characterized by the side portions being moved toward each other and at least partially in contact with each other. The apparatus may further comprise a heating element on at least one of the side portions and being configured to increase a temperature of the at least one side portion to warm a said medical implement positioned between the side portions in the pocket of the engaging structure. The apparatus may also comprise an attraction element on at least one of the side portions to causing attraction between the side portions to maintain the side portions in the operational positions of the side portions.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
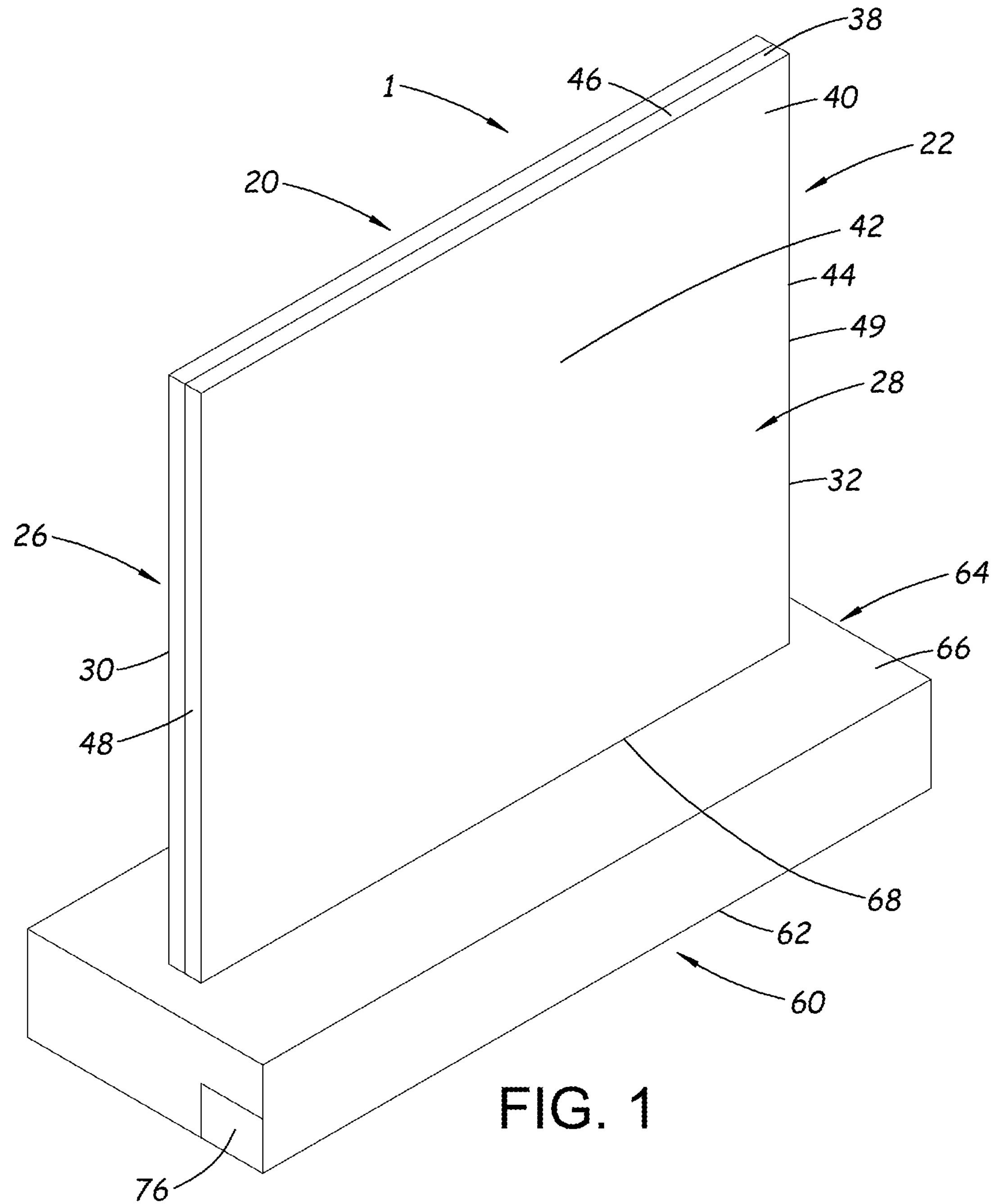
FIG. 1 is a schematic perspective view of a new apparatus for warming a medical device without a medical implement present, according to the present disclosure.
Figure 2:
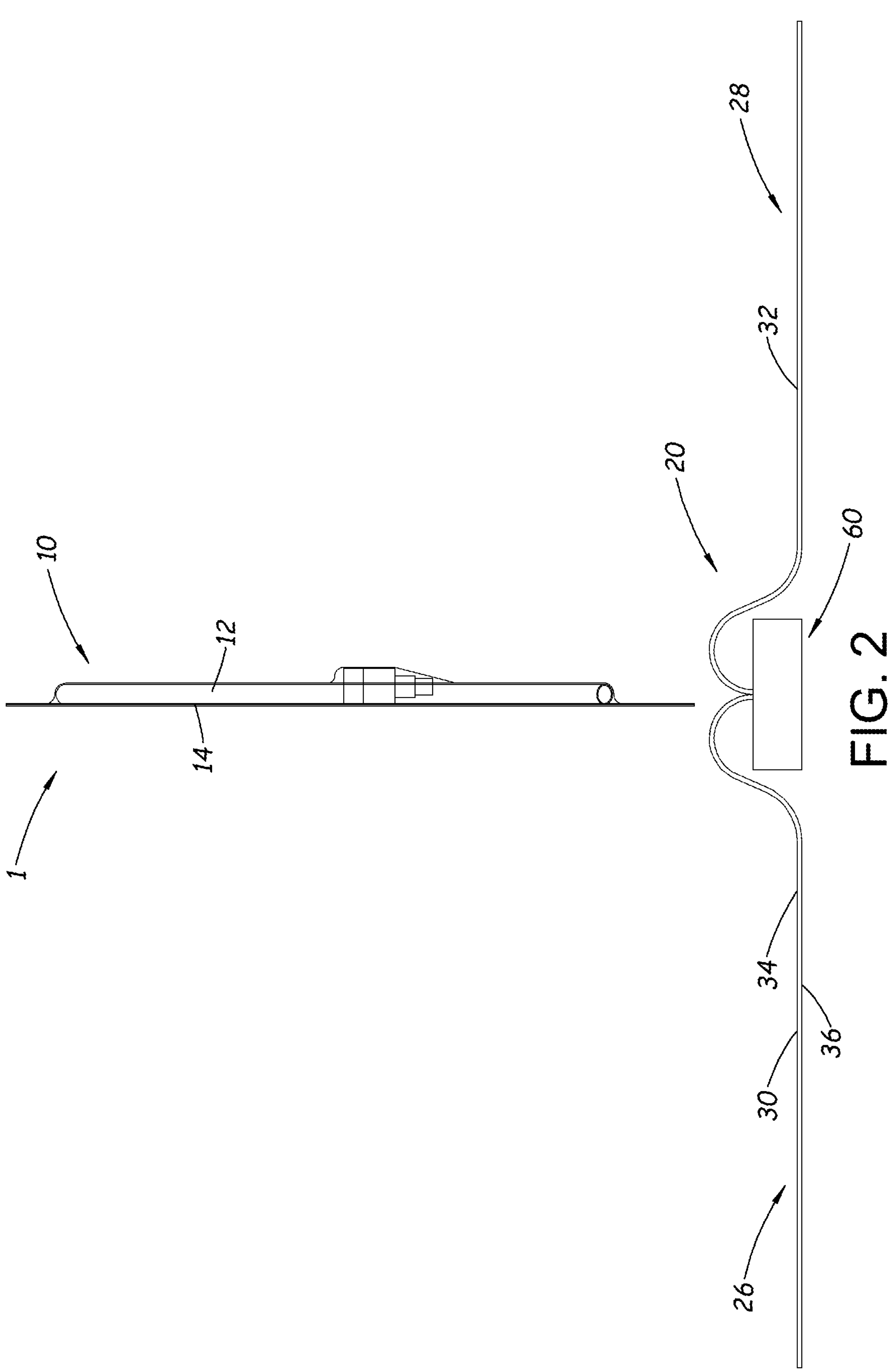
FIG. 2 is a schematic side view of the apparatus depicting the side portions of the apparatus in the receiving condition and depicting a medical implement above the apparatus prior to movement of the side portions of the apparatus to the operational condition, according to an illustrative embodiment.

With reference now to the drawings, and in particular to FIGS. 1 through 11 thereof, a new apparatus for warming a medical device prior to use that embodies the principles and concepts of the disclosed subject matter will be described.

The applicants have recognized that the use of a medical implement that has been warmed up from a typical room temperature of a medical facility may reduce or eliminate some of the possible negative side effects of the introduction of the implement into a patient's body. For example, when the implement includes a tube or conduit, such as an endotracheal tube or a nasogastric tube, the warming of the tube can reduce the incidence of nasal epistaxis, or nosebleed. Also, the applicants of recognized that the warming of medical implement tubing, and particularly double lumen tubes, can reduce intubation resistance, lower the incidence of postoperative glottic injury, and hoarseness in the patient. Additionally, the applicants of recognized that warming of an endotracheal tube can reduce the time required to successfully intubate a patient.

A system 1 of the disclosure may in some embodiments include a medical implement 10, and more specifically may include a medical implement having a part which is intended to be inserted into the body of a patient is a part of a medical procedure. Embodiments of the medical implement may comprise a medical device which includes a tubular conduit 12 for insertion into the body of the patient, such as through an orifice of the body of the patient. For example, the conduit 12 of the implement may be utilized for insertion into the nose or the mouth of the patient, although implements with conduits for use with other orifices may be useful. Illustratively, the tubular conduit 12 may comprise an endotracheal tube or a nasogastric tube. The tubular conduit 12 may be formed of a flexible material, such as, for example, a polyvinyl chloride. The tubular conduit 12 is typically elongated and flexible along a length direction of the conduit.

The medical implement 10 may broadly also include packaging 14 for the tubular conduit 12, as well as other parts appurtenant to the conduit. The packaging 14 may define an interior 16 in which the tubular conduit is positioned, as well as other parts of the implement 10. Illustratively, the packaging 14 may comprise a pair of sheets 18, 19 that extend generally parallel to each other on opposite sides of the interior 16, and may be bonded together at the peripheries of the sheets to form an airtight interior.

The system 1 of the disclosure includes an apparatus 20 for warming at least a portion of a medical implement, and the system may comprise the apparatus 20 alone or in combination with the medical implement. In general, operation of the apparatus 20 may increase the temperature of a medical implement from an ambient or room air temperature to a warmer or higher temperature. The apparatus 20 may be configured to form or define a space for receiving a least a portion of the medical implement to be warmed.

The apparatus 20 may comprise a medical implement engaging structure 22 for engaging the portion of the medical implement to be warmed and a base structure 60 for at least partially supporting the engaging structure 22. The engaging structure 20 may be configured to contact the medical implement to permit transfer of heat to the implement, and the contact may include contact with the packaging 14 of the implement when such packaging is present. The engaging structure may be configured to form a pocket 24 for receiving the medical implement, and the magnitude or volume of the space in the pocket may be varied to adjust to the magnitude or volume of the space occupied by the implement 10. In embodiments, the engaging structure 22 has the capability of adapting volume of the space of the pocket 24 generally to the volume of space occupied by the implement 10.

Figures 3, 4:
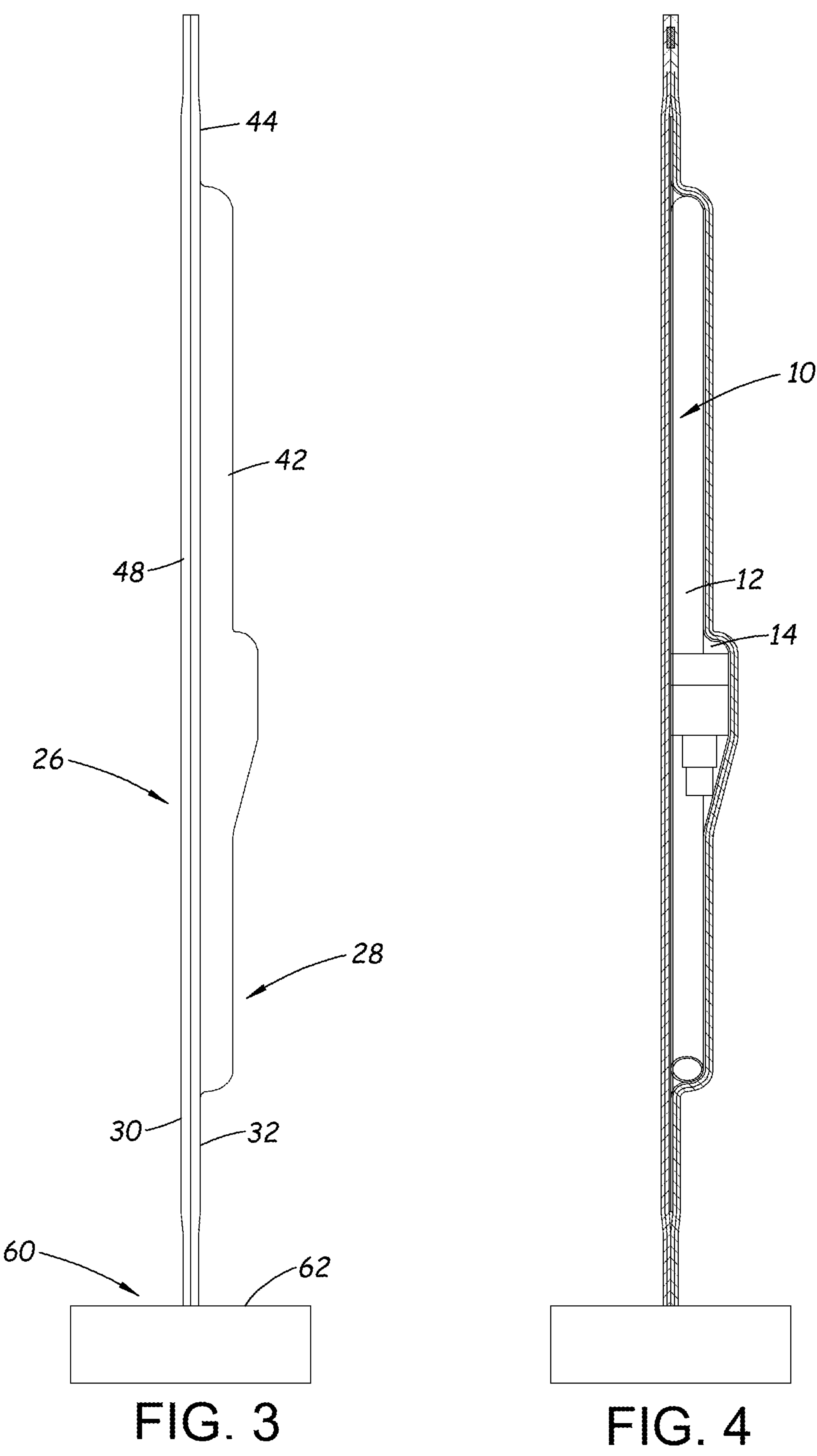
FIG. 3 is a schematic side view of the apparatus with the side portions in the operational condition and a medical implement in the pocket of the implement engaging structure, according to an illustrative embodiment.
FIG. 4 is a schematic side sectional view of the apparatus in the operational condition as depicted in FIG. 3, according to an illustrative embodiment.

The engaging structure 22 of the apparatus may have a receiving condition (see FIG. 2) and an operational condition (see FIGS. 3 and 4). The receiving condition may be characterized by the pocket 24 of the engaging structure being substantially open, and ready to receive a medical implement to be warmed, and the operational condition may be characterized by the pocket being substantially closed and in suitable configuration for warming the implement.

In embodiments of the disclosure, the implement engaging structure 22 may include a pair of side portions 26, 28 which are configured to form the pocket 24. The side portions 26, 28 may be movable with respect to each other, and may be movable with respect to the base structure 60. Illustratively, the side portions may be movable away from each other to respective receiving position (see, e.g., FIG. 2) corresponding to the receiving condition of the engaging structure. The receiving position of the side portions may thus be characterized by the side portions being separated from each other. The side portions 26, 28 may also be a movable toward each other to respective an operational position corresponding to the operational condition of the engaging structure. The operational position of the side portions 26, 28 may thus be characterized by the side portions being moved toward each other and brought together to a large degree, and the operational position be further characterized by the side portions being in contact with each other.

In the illustrative embodiments, each of the side portions 26, 28 is formed by a side panel 30, 32 which is each formed of a material. The material of at least one of the side panels, and optionally both side panels, comprises a flexible material. Further, the material forming one or more of the side panels 30, 32 may have a degree of elasticity. Each side panel has an inner surface 34, and the inner surfaces of the pair of side panels are positioned in opposition to each other in the operational positions of the panels when the engaging structure is in the operational condition. Each side panel also has an outer surface 36 opposite of the inner surface of the respective side panel. In embodiments, the side panels 30, 32 are substantially coextensive with each other in the operational position of the side portions.

Each side panel 30, 32 has a perimeter 38, and in the illustrative embodiments, the perimeter is substantially rectangular in shape although other shapes may optionally be utilized. Each side panel has a perimeter section 40 which extends along at least a portion of the perimeter 38 and has a central section 42 surrounded by at least a part by the perimeter section. Optionally, parts of the perimeter section 40 may exhibit a greater degree of rigidity than the central section, and may include a frame positioned along the perimeter section of the side panel.

Each side panel 30, 32 has a perimeter edge 44 along at least a portion of the perimeter 38 of the side panel. The perimeter section 40 of the panels may extend from the perimeter edge toward the central section 42. In embodiments of the side panels, and particularly those having a substantially rectangular shape, the perimeter edge 44 may have an upper edge portion 46 and a pair of side edge portions 48, 49. The upper edge portion 46 is illustratively located opposite of the base structure 60, and the side edge portions 40, 49 illustratively extend between the base structure and the upper edge portion 46.

At least one, and illustratively both, of the side portions 26, 28 may additionally include a heat source 50 which is configured to heat a medical implement 10 positioned between the side panels in the pocket 24 of the engaging structure. In some illustrative embodiments, the heat source 50 may be configured to cause heating of air in the pocket 24 of the apparatus. In other illustrative embodiments, the heat source 50 may be configured to cause heating of the respective side panel of one or both of the side portions, such as the inner surface 34 of the respective side panel. Thus, the heat source 50 may transfer heat to parts of the medical implement via contact with the inner surface 34 of one or both of the side panels and/or may transfer heat to the implement the contact with the air located in the pocket 24.

Figure 6:
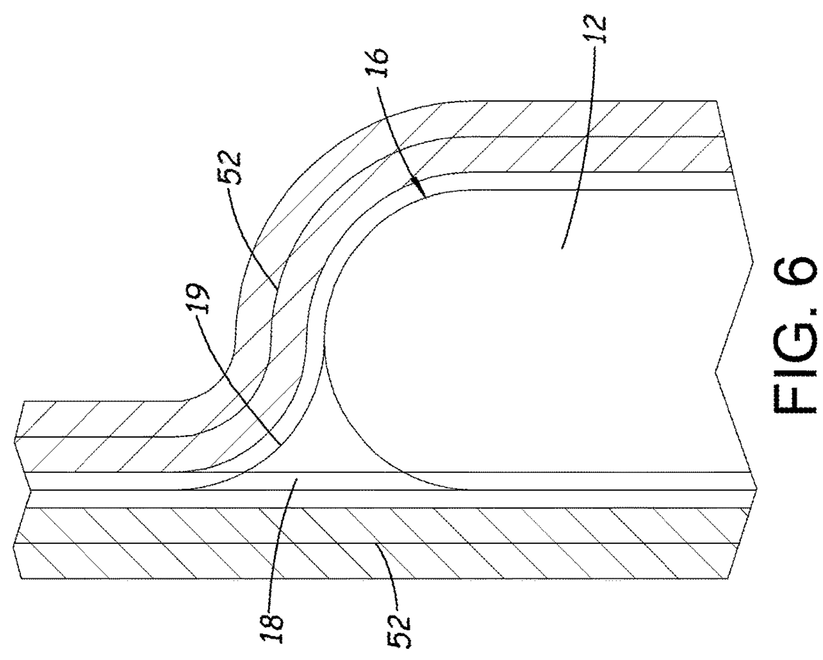
FIG. 6 is a schematic side sectional view of another enlarged portion of the apparatus shown in FIG. 4, according to an illustrative embodiment.
Figure 5:
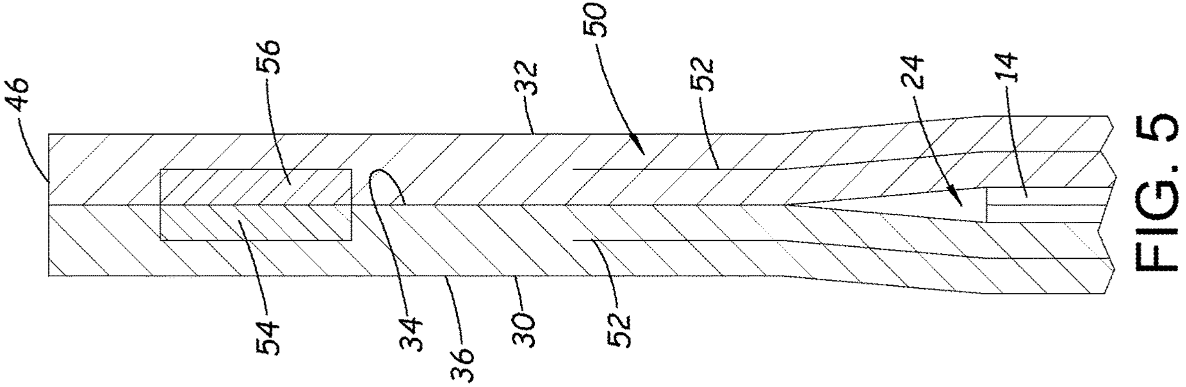
FIG. 5 is a schematic side sectional view of an enlarged portion of the apparatus shown in FIG. 4 showing positioning of the attraction elements adjacent to perimeters of the side panels, according to an illustrative embodiment.
Figure 7:
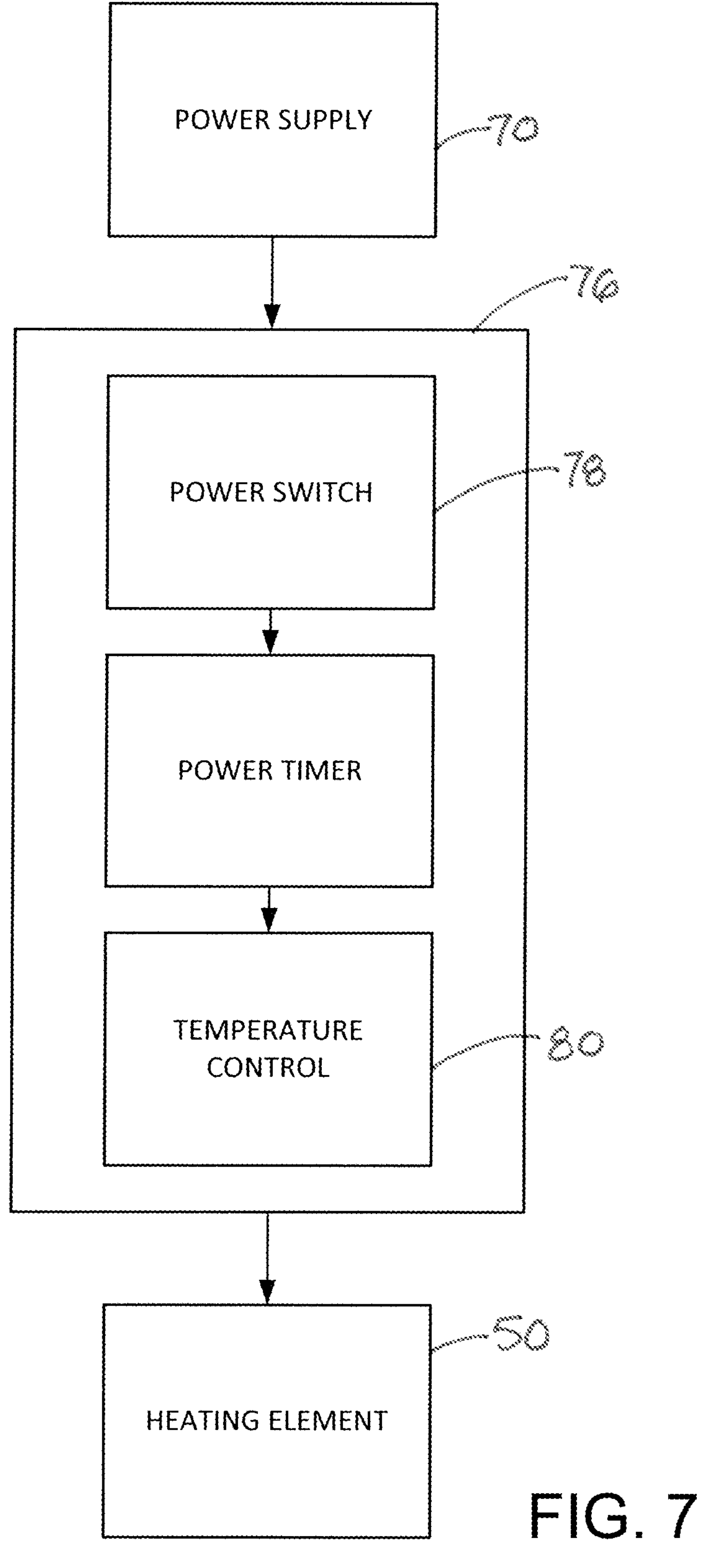
FIG. 7 is a schematic block diagram of elements of the apparatus, according to an illustrative embodiment.
Figure 8:
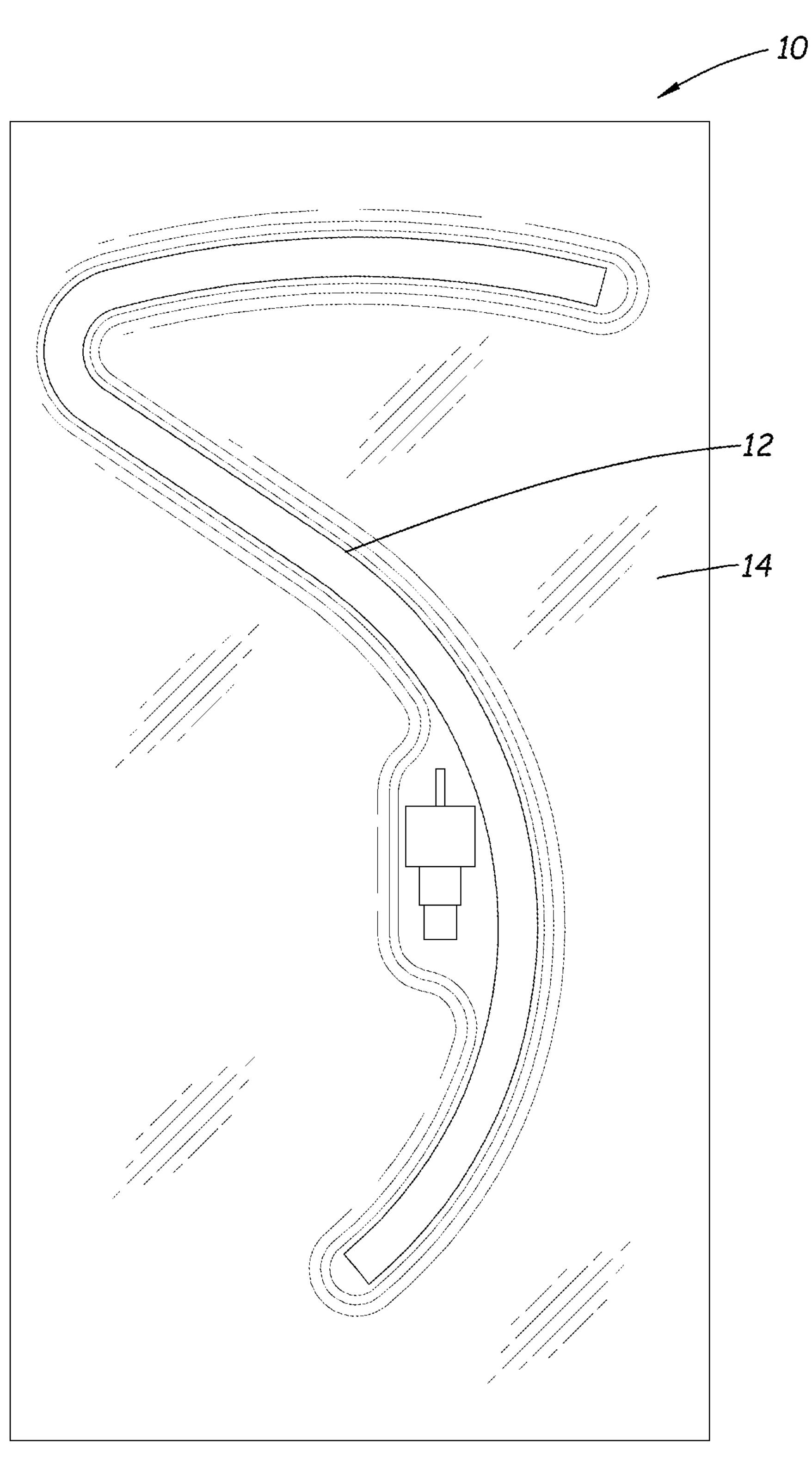
FIG. 8 is a schematic top view of an illustrative medical implement including conduit and packaging.

In some embodiments of the apparatus 10, such as shown in FIGS. 5 and 6, the heat source 50 may comprise a heating element 50 positioned on one or both of the side panels of the respective side portions, and may be positioned between the inner 34 and outer 36 surfaces. In some embodiments, the heating element 50 may be positioned on the central section 42 of the side panel, and may not be positioned on the peripheral section 40. Illustratively, the heating element 52 may comprise an electrical resistance element which heats up upon the passage of an electrical current through the resistance element, and the heat of the element may be conducted by the material of the side panel or panels to the medical implement directly in contact with the side panel and/or the air in the pocket 24 in contact with the side panel which is in turn conducted from the air to the implement.

Figures 9, 10:
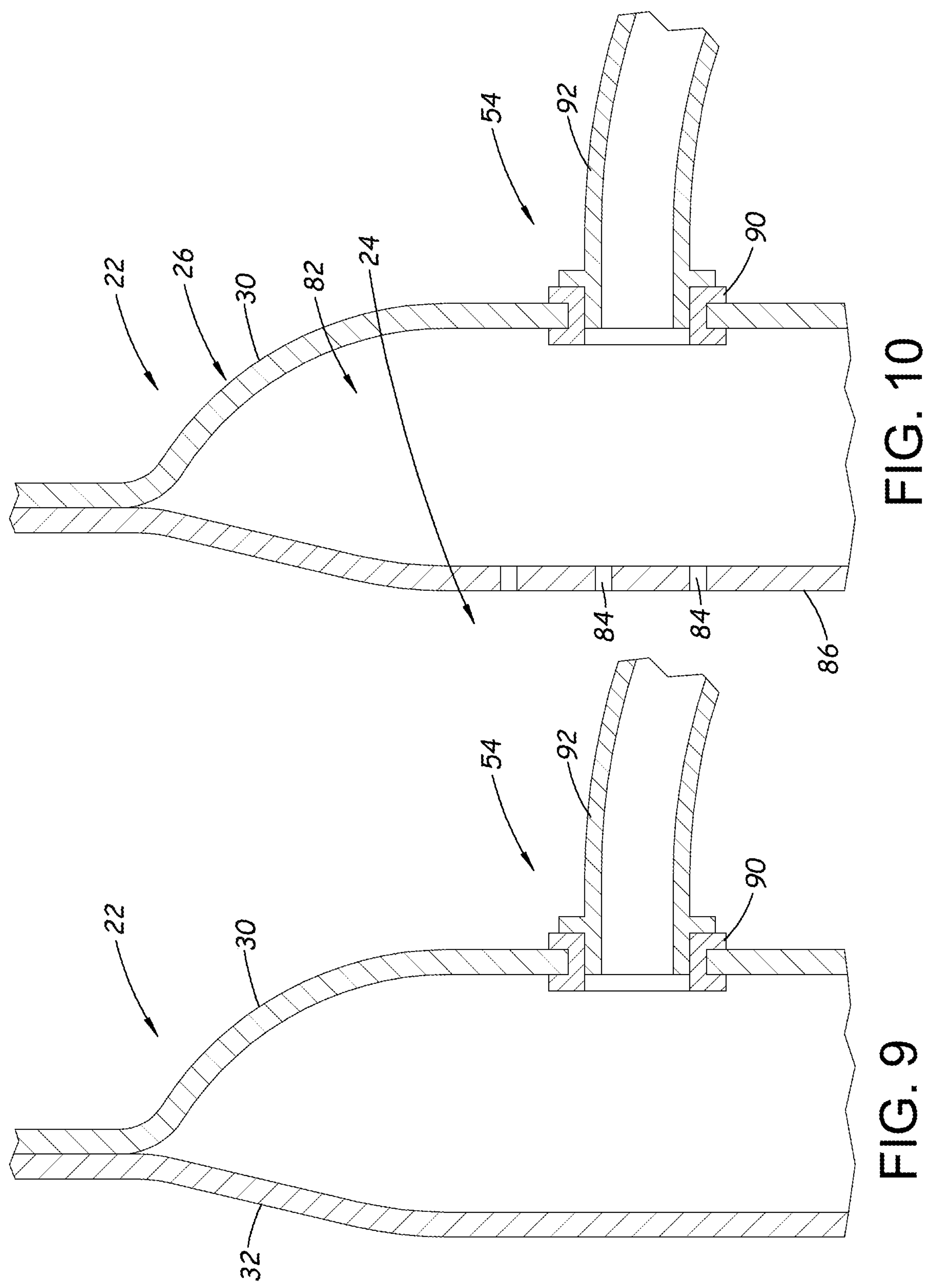
FIG. 9 is a schematic sectional view of a portion of the medical implement engaging structure showing a part of the heat source communicating heated air to the pocket of the apparatus, according to an illustrative embodiment.
FIG. 10 is a schematic sectional view of a portion of the medical implement engaging structure showing a part of the heat source communicating heated air to a cavity in one of the side panels of the engaging structure, according to an illustrative embodiment.
Figure 11:
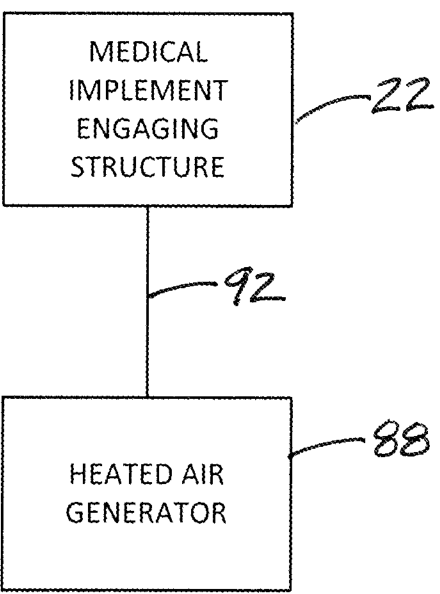
FIG. 11 is a schematic block diagram of elements of the air heating assembly of the heat source, according to an illustrative embodiment.

In some embodiments of the apparatus 10, such as shown in FIGS. 9 through 11, the heat source 50 comprises an air heating assembly 54 that is configured to transfer heated air to the implement engaging structure 22. Illustratively, the air heating assembly 54 may be configured to cause heated air to be communicated to the pocket 24 of the engaging structure, such as is illustrated in FIG. 9. In such an embodiment, air is moved or forced into the pocket 24 between the side panels in the flow of heated air may be maintained by the limited or constrained escape of air from the pocket through, for example, gaps between the perimeter edges 44 of the side panels. Also illustratively, the air heating assembly 54 may be configured to cause heated air to be communicated to a cavity 82 formed in at least one of the side panels, such as is illustrated in FIG. 10. Optionally, the heated air may be vented from the cavity in a constrained manner, or may enter the pocket from the cavity through a plurality of perforations 84 formed in the inner wall section 86 of the in the air heating assembly being in fluid communication with the cavity.

Illustrative embodiments of the air heating assembly 54 may include a heated air generator 88 configured to produce a flow of heated air. One example of a heated air generator often found in medical environments is the Bair Hugger Normothermia System available from 3M Medical of St. Paul, MN, USA. The air heating assembly 54 may also include a connection fitting 90 mounted on at least one of the side panels 30 of the engaging structure 22. In embodiments, the connection fitting 90 may be in fluid communication with the cavity 82 in the side panel (see FIG. 10), and in other embodiments the connection fitting may extend through the side panel 30 to be in fluid communication with the pocket 24 of the engaging structure (see FIG. 9). Further, the air heating assembly 54 may further include a conduit 92 connecting the heated air generator 88 to the connection fitting 90, and illustratively the conduit comprises flexible tubing.

The side portions 26, 28 may additionally comprise an attraction element 52 which causes attraction between the side panels to effectively hold the side panels together in their operational positions of the operational condition, while permitting the side panels to be separated and moved toward the receiving positions of the receiving condition. The attraction element 52 may comprise a plurality of attraction elements 52, 54 which may be mounted on each of the side panels, and at various locations on the side panels. In embodiments, each of the attraction elements 52, 54 may be located toward the perimeters 38 of the side panels. In the illustrative embodiments, the attraction elements are located along the side edge portions 48, 49 of the respective side panels, and in some embodiments the attraction elements are also located along the upper edge portions 46 of the respective side panels. Illustratively, each of the attraction elements 52, 54 comprises a magnetically-active item, so that the magnetically active items of one 30 of the side panels is attracted to the magnetically active items of the other one 32 of the side panels. The magnetically active item or items may comprise a discrete magnet or magnets, or optionally a magnet with an elongated form extending along one of the edge portions of the side panel.

The attraction elements may be suitably positioned on the side panels to magnetically pull the perimeter sections of the respective side panels together while the medical implement is positioned in the pocket to maximize contact between the side panels and the medical implement and thus enhance the communication of heat from the heating element or elements of the side panels to the implement in the pocket. Illustratively, the magnetically active items may be positioned along the sections of the perimeter portion at substantially uniform spacings or may extend continuously or substantially continuously along the sections.

The base structure 60 of the apparatus may be configured for positioning on a surface to support the apparatus and support the engaging structure above the surface. The base structure may include a housing 62. The side portions 26, 28 of the engaging structure 22 may extend from a top 64 of the housing. The housing 62 may have a top wall 66 with an elongate opening 68 from which the side panels 30, 32 extend. The housing 62 may also have a bottom wall and a perimeter wall extending between the top and bottom walls to define an interior of the housing.

The apparatus 20 may also include a power supply 70 which may be positioned in the interior of the housing 62. In embodiments, the power supply 70 may comprise a battery power source, such as a replaceable single use battery or a rechargeable multiple use battery. In some embodiments, the power supply 70 may comprise a power cord which is connectable to a structural power circuit via an electrical outlet. The apparatus may further include operational controls 76 for controlling the operation of aspects of the apparatus, such as the heating element 50. Illustratively, the operational controls 76 may include a power switch 78 to control the operational status of the apparatus (e.g., either "ON" or "OFF"), and may include a temperature control 80 for variably controlling the magnitude of the electrical power being supplied to the heating element supplied to the adjust the amount of heat produced by the heating element and thereby communicated to a medical implement. Illustratively, discrete temperature settings may be provided such as, for example, 40 degrees C., 45 degrees C. and 50 degrees C. The controls 76 may also include a timer with adjustability to set a particular period of warming of the implement by the heating element of the apparatus before the heating element is turned off. As a further option, automatic power shut off functionality may be provided to cause the apparatus to turn its power off after a period to save energy.

Any suitable material with a flexible characteristic may be utilized for the side panels 30, 32, and materials with antimicrobial characteristics may be highly useful. Further, a non-porous material for the panels may be preferable for enhancing the ability to clean the panels between uses, such as by wiping down with antimicrobial wipes.

In a method of use of the apparatus, the medical implement 10 to be utilized in a medical procedure is placed in the apparatus 20 by positioning the implement above the base structure 60 while the engaging structure 22 is in the receiving condition with the side panels 30, 32 in their respective receiving positions. The side panels are moved from the receiving positions toward each other to the operational positions of the panels with the implement 10 positioned between the panels. The perimeter sections of the panels may be brought together by the attraction of the attraction elements 52, 54 to each other to help hold the sections of the side panels together with the implement 10 in between. The operational controls 76 of the apparatus may be manipulated to provide power to the heating element 50 and the amount of power supplied to the heating element may be adjusted to achieve the desired degree of warming of the implement. The heating element may cause at least the inner surfaces 34 of the side panels to heat up and directly transfer heat to the medical implement through contact (e.g., conduction), but may also transfer heat indirectly to the implement by heating air in the pocket 24 between the side portions (e.g., convection).

It should be appreciated that in the foregoing description and appended claims, that the terms "substantially" and "approximately," when used to modify another term, mean "for the most part" or "being largely but not wholly or completely that which is specified" by the modified term, and may be further quantified as values or qualities which deviate approximately 10 percent or less from the value or quality or relationship stated in the disclosure.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that steps set forth in the description and/or shown in the drawing figures may be altered in a variety of ways. For example, the order of the steps may be rearranged, substeps may be performed in parallel, shown steps may be omitted, or other steps may be included, etc.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:

1. A system comprising:

an apparatus for warming at least a portion of a medical implement, the apparatus comprising:

a medical implement engaging structure for engaging the portion of the medical implement to permit transfer of heat to the implement, the engaging structure being configured to form a pocket for receiving the medical implement, the engaging structure having a receiving condition and an operational condition, the receiving condition being characterized by the pocket being substantially open, the operational condition being characterized by the pocket being substantially closed, the implement engaging structure comprising:

a pair of side portions configured to form the pocket, the side portions being movable with respect to each other, the side portions each having a receiving position corresponding to the receiving condition of the engaging structure, the side portions each having an operational position corresponding to the operational condition of the engaging structure, the receiving position of the side portions being characterized by the side portions being separated and moved away from each other, the operational position of the side portions being characterized by the side portions being moved toward each other and at least partially in contact with each other, each of the side portions comprising a side panel with an inner surface, the operational position of the side portions being further characterized by the inner surface of at least one of the side panels being configured to contact a said medical implement when the medical implement is positioned in the pocket;

a heat source configured to warm a said medical implement positioned between the side portions in the pocket of the engaging structure, the heat source being associated with at least one of the side panels such that heat from the heat source is transferred to the at least one side panel and to a said medical implement positioned in the pocket and contacted by the at least one side panel; and an attraction element on at least one of the side portions to cause attraction between the side portions to maintain the side portions in the operational positions of the side portion;

wherein the at least one side panel is formed of a flexible material such that the at least one side panel flexes with contact of the inner surface of the at least one side panel with a said medical implement when the medical implement is positioned in the pocket and the at least one side panel is in the operational position.

2. The system of claim 1 wherein the flexible material of the at least one of the side panels is a material with elasticity such that the at least one side panel stretches to form the pocket in the operational condition of the implement engaging structure.

3. The system of claim 1 wherein each of the side panels is formed of the flexible material.

4. The system of claim 1 wherein the side panels are substantially coextensive with each other in the operational position.

5. The system of claim 1 wherein each of the side panels has a perimeter, each of the side panels having a perimeter section extending along at least a portion of the perimeter, each of the side panels further having a central section surrounded at least in part by the perimeter section; and wherein the heat source comprises a heating element on at least one side portion of the medical implement engaging structure, the heating element of the at least one side portion being located on the central section of the side panel of the side portion.

6. The system of claim 1 wherein the attraction element comprises a plurality of attraction elements, at least one of the attraction elements being mounted on each of the side panels.

7. The system of claim 6 wherein the attraction elements are located toward perimeters of each of the side panels.

8. The system of claim 6 wherein each of the attraction elements comprises a magnet.

9. The system of claim 1 wherein the apparatus additionally comprises a base structure for supporting the medical implement engaging structure on a surface, the base structure including a power supply.

10. The system of claim 1 wherein the apparatus additionally comprises operational controls for controlling operation of the heat source of the apparatus.

11. The system of claim 1 additionally comprising said medical implement, the medical implement being removably positioned in the pocket of the medical implement engaging structure between the side portions of the engaging structure.

12. The system of claim 11 wherein the medical implement includes a tubular conduit configured to be inserted into an orifice of a body of a patient.

13. The system of claim 12 wherein the medical implement includes packaging defining an interior, the tubular conduit being positioned in the interior of the packaging.

14. The system of claim 1 wherein the heat source comprises a heating element on at least one side portion of the medical implement engaging structure.

15. The system of claim 14 wherein the heating element comprises an electrical resistance element.

16. A system comprising:

an apparatus for warming at least a portion of a medical implement, the apparatus comprising:

a medical implement engaging structure for engaging the portion of the medical implement to permit transfer of heat to the implement, the engaging structure being configured to form a pocket for receiving the medical implement, the engaging structure having a receiving condition and an operational condition, the receiving condition being characterized by the pocket being substantially open, the operational condition being characterized by the pocket being substantially closed, the implement engaging structure comprising:

a pair of side portions configured to form the pocket, the side portions being movable with respect to each other, the side portions each having a receiving position corresponding to the receiving condition of the engaging structure, the side portions each having an operational position corresponding to the operational condition of the engaging structure, the receiving position of the side portions being characterized by the side portions being separated and moved away from each other, the operational position of the side portions being characterized by the side portions being moved toward each other and at least partially in contact with each other, each of the side portions comprising a side panel with an inner surface, the operational position of the side portions being further characterized by the inner surface of at least one of the side panels being configured to contact a said medical implement when the medical implement is positioned in the pocket;

a heat source configured to warm a said medical implement positioned between the side portions in the pocket of the engaging structure;

elements on the side portions to selectively maintain the side portions in the operational positions of the side portions;

wherein the at least one side panel is formed of a flexible material such that the at least one side panel flexes with contact of the inner surface of the at least one side panel with a said medical implement when the medical implement is positioned in the pocket and the at least one side panel is in the operational position; and, wherein the heat source comprises an air heating assembly configured to provide heated air to heat a said medical implement in the medical implement engaging structure, the air heating assembly including a heated air generator configured to generate heated air and communicate the heated air to the interior of the pocket and a said medical implement positioned in the pocket when a said medical implement is positioned in the pocket.

17. A system comprising:

an apparatus for warming at least a portion of a medical implement, the apparatus comprising:

a medical implement engaging structure for engaging the portion of the medical implement to permit transfer of heat to the implement, the engaging structure being configured to form a pocket for receiving the medical implement, the engaging structure having a receiving condition and an operational condition, the receiving condition being characterized by the pocket being substantially open, the operational condition being characterized by the pocket being substantially closed, the implement engaging structure comprising:

a pair of side portions configured to form the pocket, the side portions being movable with respect to each other, the side portions each having a receiving position corresponding to the receiving condition of the engaging structure, the side portions each having an operational position corresponding to the operational condition of the engaging structure, the receiving position of the side portions being characterized by the side portions being separated and moved away from each other, the operational position of the side portions being characterized by the side portions being moved toward each other and at least partially in contact with each other, each of the side portions comprising a side panel with an inner surface, the operational position of the side portions being further characterized by the inner surfaces of the side panels being configured to contact a said medical implement when the medical implement is positioned in the pocket;

a heat source configured to warm a said medical implement positioned between the side portions in the pocket of the engaging structure, the heat source being associated with at least one of the side panels such that heat from the heat source is transferred to the at least one side panel and to a said medical implement positioned in the pocket and contacted by the at least one side panel, the heat source comprising a heating element on the at least one side panel of the medical implement engaging structure;

an attraction element on at least one of the side portions to cause attraction between the side portions to maintain the side portions in the operational positions of the side portion;

wherein each of the side panels is formed of a flexible material such that the side panels flex with contact of the inner surfaces of the side panels with a said medical implement when the medical implement is positioned in the pocket and the side panels are in the operational position.

18. The system of claim 17 wherein the flexible material of the side panels is a material with elasticity such that the side panels stretch to form the pocket about the said medical implement in the operational condition of the implement engaging structure.

19. The system of claim 17 wherein the apparatus additionally comprises operational controls for controlling operation of the heat source of the apparatus.

* * * * *